(12) United States Patent
Bailey et al.

(10) Patent No.: US 8,049,638 B2
(45) Date of Patent: *Nov. 1, 2011

(54) SENSOR FOR DETECTING HYDROCARBONS

(75) Inventors: Douglas S. Bailey, Deerfield, IL (US); Steven Kubicek, Schaumburg, IL (US)

(73) Assignee: Perma-Pipe, Inc., Niles, IL (US)

( * ) Notice: Subject to any disclaimer, the term of this patent is extended or adjusted under 35 U.S.C. 154(b) by 478 days.

This patent is subject to a terminal disclaimer.

(21) Appl. No.: 12/279,698

(22) PCT Filed: Feb. 13, 2007

(86) PCT No.: PCT/US2007/003946
§ 371 (c)(1),
(2), (4) Date: Aug. 15, 2008

(87) PCT Pub. No.: WO2007/097974
PCT Pub. Date: Aug. 30, 2007

(65) Prior Publication Data
US 2011/0041588 A1    Feb. 24, 2011

(51) Int. Cl.
*G08B 3/00* (2006.01)
(52) U.S. Cl. .............. 340/691.1; 340/539.22; 340/603; 204/401
(58) Field of Classification Search ........... 340/691.1, 340/506, 539.22, 603; 73/53.01; 204/401, 204/421, 415, 422, 423
See application file for complete search history.

(56) References Cited

U.S. PATENT DOCUMENTS

| | | |
|---|---|---|
| 3,204,872 A | 9/1965 | Whear |
| 3,808,385 A | 4/1974 | Klinefelter |
| 3,874,223 A | 4/1975 | Miyazaki et al. |
| 4,132,616 A | 1/1979 | Tantram et al. |
| 4,631,952 A | 12/1986 | Donaghey |
| 4,728,882 A | 3/1988 | Stanbro et al. |
| 4,743,954 A | 5/1988 | Brown |
| 4,855,706 A | 8/1989 | Hauptly |
| 4,926,165 A | 5/1990 | Lahlouh et al. |
| 4,972,179 A | 11/1990 | Akiba |
| 5,057,430 A | 10/1991 | Newman |
| 5,101,083 A | 3/1992 | Tyler et al. |
| 5,256,574 A | 10/1993 | Neuburger et al. |
| 5,341,128 A | 8/1994 | Keyser et al. |
| 5,468,374 A | 11/1995 | Knoll |
| 5,482,678 A | 1/1996 | Sittler |

(Continued)

OTHER PUBLICATIONS

International Search Report from co-pending PCT/US07/03946 mailed Jul. 17, 2008.

*Primary Examiner* — Daryl Pope
(74) *Attorney, Agent, or Firm* — Ungaretti & Harris LLP

(57) ABSTRACT

A fluid sensor comprises a sensor housing, a sensor package, an actuator and a switch. The sensor package is disposed within the sensor housing and includes first and second screens and at least one sensing membrane. The sensing membrane is disposed between the first and second screens and is adapted to expand when exposed to a predetermined quantity of a first predetermined fluid. The actuator is disposed proximate the sensor package within the sensor housing and moveable between a first position and a second position through an intermediate position. The switch is disposed proximate the actuator and is operable between closed and open positions. When the actuator is in the second position at least a portion of the actuator depresses the switch to control an electrical circuit connected therewith.

22 Claims, 3 Drawing Sheets

U.S. PATENT DOCUMENTS

| | | | |
|---|---|---|---|
| 5,514,338 A | 5/1996 | Simon et al. |
| 5,661,405 A | 8/1997 | Simon et al. |
| 5,666,096 A | 9/1997 | Van Zeeland |
| 5,783,747 A | 7/1998 | Lindow et al. |
| 5,796,097 A | 8/1998 | Lawrence |
| 5,817,727 A | 10/1998 | Prass et al. |
| 5,898,101 A | 4/1999 | Lyle et al. |
| 5,990,772 A | 11/1999 | Van Zeeland |
| 6,007,776 A | 12/1999 | Matsumoto |
| 6,010,616 A | 1/2000 | Lewis et al. |
| 6,032,536 A | 3/2000 | Peeters et al. |
| 6,044,717 A | 4/2000 | Biegelsen et al. |
| 6,130,593 A | 10/2000 | Van Zeeland |
| 6,200,443 B1 | 3/2001 | Shen et al. |
| 6,433,694 B1 | 8/2002 | Dolan et al. |
| 6,568,286 B1 | 5/2003 | Cabuz |
| 6,758,107 B2 | 7/2004 | Cabuz |
| 6,778,918 B2 | 8/2004 | Delhomme et al. |
| 6,823,718 B2 | 11/2004 | Sandford et al. |
| 6,849,239 B2 | 2/2005 | Morris |
| 6,852,216 B2 | 2/2005 | Moscaritolo et al. |
| 6,889,567 B2 | 5/2005 | Cabuz |
| 6,896,781 B1 | 5/2005 | Shen et al. |
| 7,037,277 B1 | 5/2006 | Smith et al. |
| 7,384,396 B2 | 6/2008 | Samuels et al. |
| 7,525,444 B2 * | 4/2009 | Bailey et al. ............... 340/691.1 |
| 2004/0020422 A1 | 2/2004 | Tsengas |
| 2005/0262943 A1 | 12/2005 | Claydon et al. |
| 2007/0281288 A1 | 12/2007 | Belkin et al. |

* cited by examiner

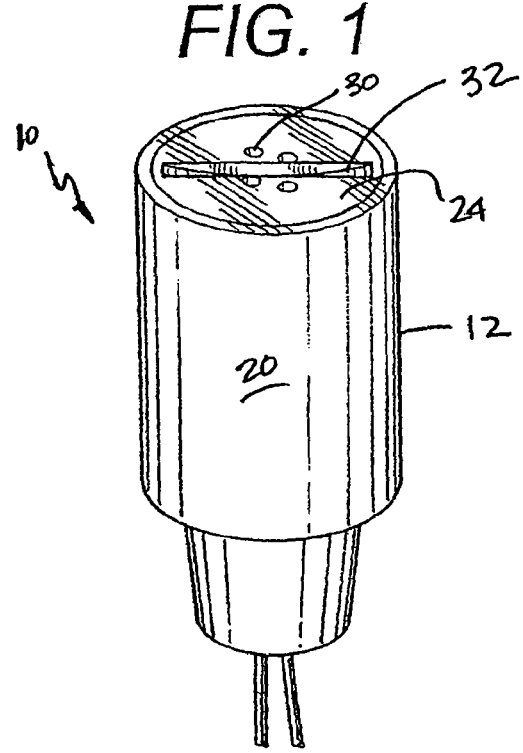
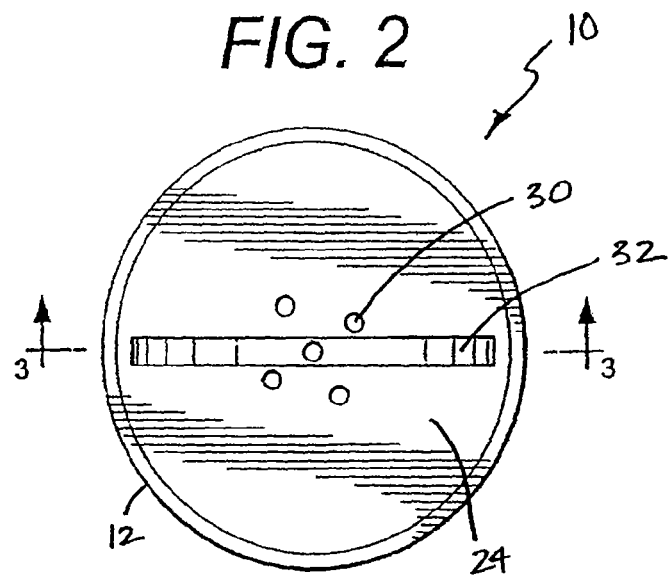
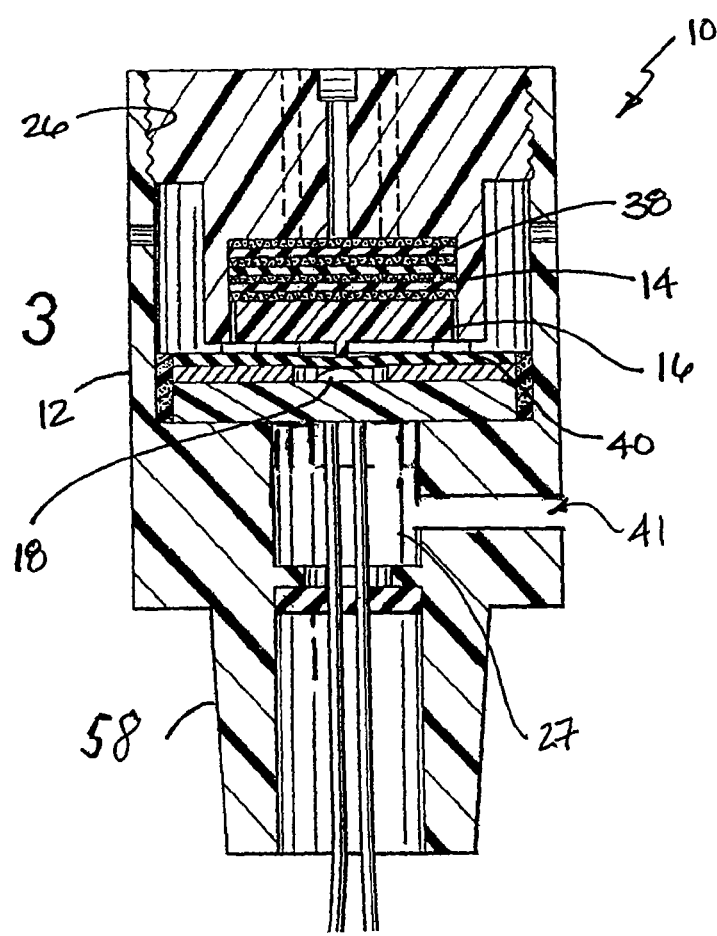

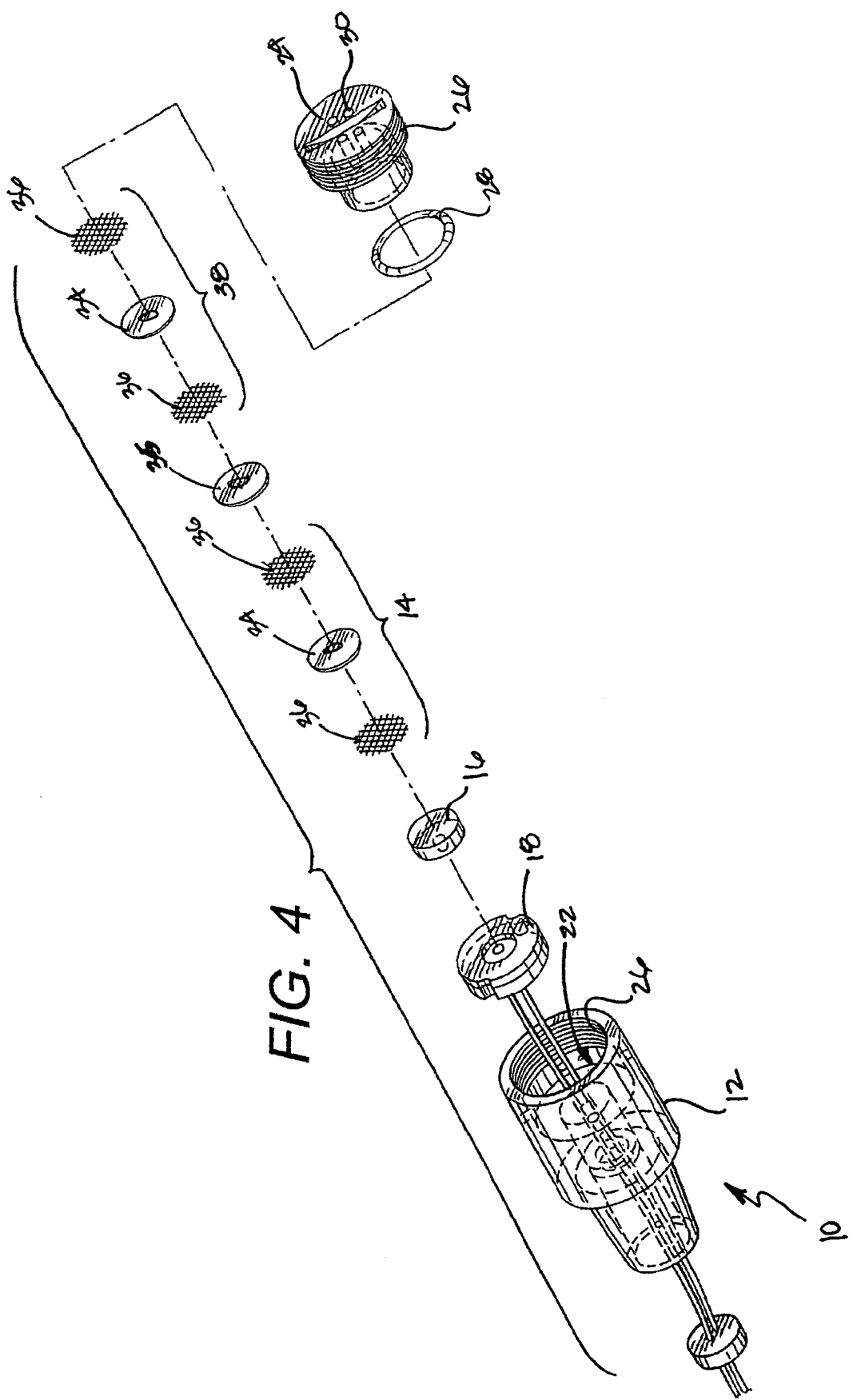

SENSOR FOR DETECTING HYDROCARBONS

CROSS-REFERENCE TO RELATED APPLICATIONS

This application is a United States National Stage Application under 35 U.S.C. Section 371 of International Patent Application No. PCT/US2007/003946 filed on Feb. 13, 2007, which claims the priority benefit of U.S. application Ser. No. 11/357,907 filed on Feb. 17, 2006, now U.S. Pat. No. 7,525,444, both of which are hereby incorporated by reference as if fully set forth herein.

TECHNICAL FIELD

The invention relates to a sensor for detecting volatile fluids, and more particularly, to a sensor for detecting hydrocarbons and triggering an alert or alarm when hydrocarbons are detected.

BACKGROUND OF THE INVENTION

Hydrocarbon liquid sensor probes have traditionally been installed in the interstitial space of double-wall tanks and pipes, sumps, fuel hydrant pits, berms encircling aboveground tanks, groundwater monitoring wells and other locations where hydrocarbon leaks or spills may occur and accumulate. These hydrocarbons are typically fuels, solvents and chemical reagents. Such sensors are typically coupled with an alarm system that will sound an alarm upon the sensor's detection of the hydrocarbon in the immediate environment.

Some known hydrocarbon sensors generally operate on the principle of an electrical circuit, namely the sensor's circuit remains open while no hydrocarbons are detected and the sensor's circuit closes upon the detection of hydrocarbons. Specifically, such hydrocarbon sensors are typically formed of cooperative conductors forming an open circuit. Hydrocarbons cause a change in the electrical status of the conductors, thereby closing the circuit. Accordingly, the leaking hydrocarbon is detected by a signal being generated as a result of the completed circuit. In particular, such hydrocarbon sensors have been known to operate on the principle that a silicone and conductive particle matrix will swell when exposed to hydrocarbons, changing the resistance of the matrix. In these hydrocarbon sensors, the sensor operates like a switch.

One example of such a hydrocarbon sensor is described in U.S. Pat. No. 4,926,165 wherein the sensor contains a swellable material which when engorged, causes an electrical connection between two conductors. U.S. Pat. No. 4,972,179 employs a three conductor configuration to form a Wheatstone bridge circuit when the second and third conductors are short circuited by the presence of a liquid.

Another example of a hydrocarbon sensor is the one described in U.S. Pat. No. 4,855,706. That patent is directed to an electrical sensor and sensor material for detecting the presence of an organic liquid by contact that is not sensitive to the presence of organic vapors from the liquid. The sensor material includes a relatively large concentration of electrically conductive particles within a swellable matrix. U.S. Pat. No. 5,514,338 also is directed to a device for sensing liquid hydrocarbons. In U.S. Pat. No. 5,514,338, a ribbon-like sensor is employed, which has an inner, silicone rubber layer and an outer, silicone rubber layer and which has two broad faces and two narrow edges. The silicone rubber layers are capable of absorbing and swelling in the presence of a liquid hydrocarbon.

While all of these hydrocarbon sensors have met with a degree of success, they also have several deficiencies. For example, known hydrocarbon sensors cannot typically be reset after exposure to non-volatile fuels such as diesel fuel, jet fuel, crude oil and #6 fuel oil. Additionally, to the extent they can be reset, there are typically a finite number of exposures before the expansion/contraction cycle of the silicone matrix loosens the bond between the thin matrix film and the substrate therein. As such, there is a limit to these sensors' use. Many installations require annual activation tests to verify the sensor is functional; this reduces the life/reset ability of the sensor. Further, prior silicone sensor elements with conductive material therein are fragile, particularly when they become saturated with hydrocarbon liquid. This can result in a delaminating of the silicone from the associated substrate. Moreover, long-term exposure to water can damage the fragile sensor element or the substrate to which the sensor element is attached.

The present invention is provided to solve the problems discussed above and other problems, and to provide advantages and aspects not provided by prior sensors of this type. A full discussion of the features and advantages of the present invention is deferred to the following detailed description, which proceeds with reference to the accompanying drawings.

SUMMARY OF THE INVENTION

According to the present invention, a fluid sensor is provided. Very generally, the detector includes a housing with a slot and threaded top for easy access to the inside of the housing. A plurality of silicone wafers is stacked within the housing with mesh or screens disposed between each silicone wafer. Holes are provided within the top for ingress of hydrocarbons. Upon the introduction of hydrocarbons into the housing, the mesh disburses the hydrocarbons and the silicone wafers swell or expand. The stacking of wafers permits faster response or longitudinal expansion within the housing. Upon expansion, the stacked wafers physically move a mechanical actuator. The actuator is physically in communication with a switch (a low force or pressure membrane-type switch) having electrical contacts in communication with a corresponding circuit. In a preferred embodiment, the circuit connected to the device is normally closed thereby allowing current and signals to pass through the circuit and be monitored. Upon physically moving the actuator, the switch is triggered, opening up the circuit to stop any signal from passing though the circuit. In the alternative, movement of the actuator can cause the switch to close a normally open circuit permitting a signal to pass through the circuit. In short, the stack of wafers controls a switch. In the preferred embodiment, no pressure (and no swelling of the stack of wafers) keeps the circuit closed. Put another way, the switch will only stay closed while the wafers are not swollen and a hydrocarbon is not present in the device. Accordingly, in a preferred embodiment, the switch is normally closed and a current and signal can pass through the circuit. When a hydrocarbon is present in the device, the silicone swells and applies force to the switch and opens the circuit. As noted, typically, there is no pressure on the switch by the silicone wafers in the normal, dry condition.

Alternatively, the fluid sensor may include a normally open switch, which is closed by an element that dissolves in the presence of a liquid. The element initially presses on the switch to hold it closed until it dissolves.

As to specifics, the fluid sensor is comprised of a sensor housing, a first sensor package, an actuator and a switch. The first sensor package is disposed within the sensor housing and includes a first screen and a second screen. The sensor package further includes a sensing membrane disposed between the first and second screens. The sensing membrane is adapted to expand when exposed to a predetermined quantity of a first predetermined fluid. The actuator is disposed proximate the sensor package within the sensor housing. The actuator moves between a first position and a second position through an intermediate position. The switch disposed proximate the actuator operates between open and closed positions. When the actuator is in the second position, at least a portion of the actuator depresses (or depressed) the switch.

According to a further aspect of the present invention, the sensing membrane is silicone with a thickness between about 0.005 to approximately 0.250 inches and preferably between about 0.010 and 0.10 inches. It will be understood, however, that the sensing membrane may include a dissolvable element that has a thickness of greater than 0.250 inches. According to another aspect of the present invention, the sensing membrane is adapted to dissolve when exposed to a second predetermined fluid. According to yet another aspect, the sensor housing includes a body portion and a cap. The removable cap is attached to the body portion and includes a plurality of apertures therein.

According to still another aspect of the present invention, the sensor further includes a means for biasing the switch to one of either the open position or the closed position. In one embodiment of the invention, the means for biasing the switch is a magnet disposed between the actuator and the switch.

According to yet still another aspect of the present invention, the chamber below the switch includes at least one vent opening therein. In one embodiment, at least one vent opening is disposed below the switch. The fluid sensor further includes a sealing member that is hydrophobic, oleophobic or both. In such an embodiment, the sealing membrane is disposed over the vent opening, which leads to the cavity below 18. This configuration assists in equalizing the pressure or vacuum between the inside and outside of the probe assembly for pressurized or vacuum applications, respectively.

According to yet another aspect of the present invention, the sensor includes a second sensor package disposed within the sensor housing. The second sensor package is comprised of third and fourth screens. A sensing membrane is disposed between the third and fourth screens and is adapted to expand when exposed to a predetermined quantity of a first predetermined fluid. An intermediate sensor membrane is disposed between the fourth screen of the second sensor package and the first screen of the first sensor package.

A fluid sensor for detecting hydrocarbons is also provided. Again, the sensor is comprised of a sensor housing, a first sensor package, an actuator and a switch. The first sensor package is disposed within the sensor housing and includes a first screen and a second screen and a silicone membrane disposed between the first and second screens; the silicone membrane is adapted to expand when exposed to a predetermined quantity of hydrocarbon. The membrane also includes at least one aperture defining a fluid path therethrough. In one embodiment, the aperture or apertures have a diameter ($D_s$) of approximately 0.0625 inches to about 0.125 inches. The actuator is disposed proximate the sensor package and within the sensor housing and moves between a first position and a second position through an intermediate position. The switch disposed proximate the actuator operates between an open and closed position. When the actuator is in the second position, at least a portion of the actuator moves the switch from the closed position to the open position.

According to another aspect, the first and second screens are made of fiberglass, stainless steel, nylon or any other material to create a gap between the silicone sensing membrane layers.

Other features and advantages of the invention will be apparent from the following specification taken in conjunction with the following drawings.

BRIEF DESCRIPTION OF THE DRAWINGS

To understand the present invention, it will now be described by way of example, with reference to the accompanying drawings in which:

FIG. 1 is a perspective front view of the sensor made according to the teachings of the present invention;

FIG. 2 is a top plan view of the sensor shown in FIG. 1;

FIG. 3 is a side cross-sectional view of the sensor shown in FIG. 1 as taken along line 3-3 in FIG. 2; and, FIG. 4 is an exploded view of the sensor shown in FIG. 1; and, FIG. 5 is a side cross-sectional view of the sensor with additional components added to FIG. 1 for venting purposes.

DETAILED DESCRIPTION

Figure 5:
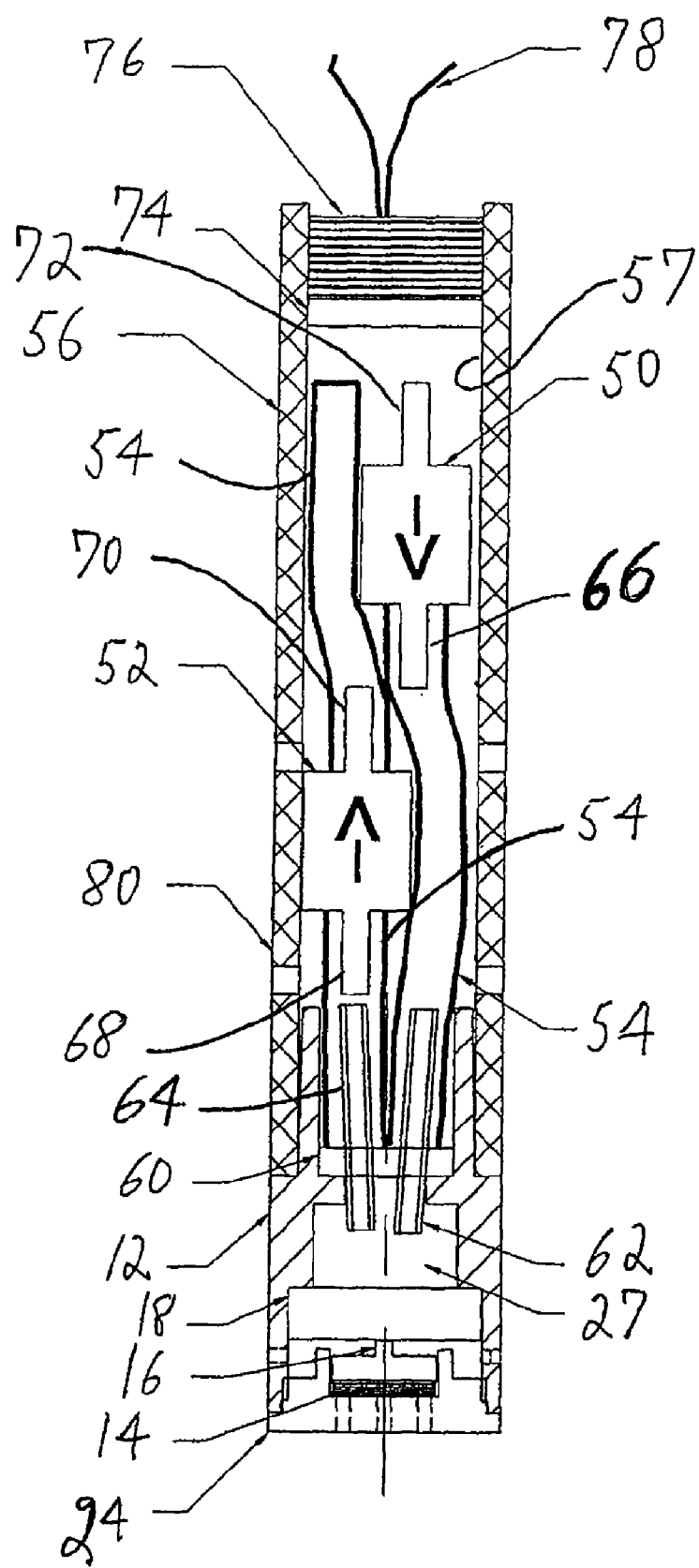

While this invention is susceptible of embodiments in many different forms, there is shown in the drawings and will herein be described in detail preferred embodiments of the invention with the understanding that the present disclosure is to be considered as an exemplification of the principles of the invention and is not intended to limit the broad aspect of the invention to the embodiments illustrated.

The present invention is a fluid sensor and, more particularly, a sensor for detecting hydrocarbons. Specifically, the sensor detects hydrocarbon by exposing thin sheets of silicone arranged within the sensor's housing to a liquid containing hydrocarbons. Exposure of the silicone to hydrocarbons causes the silicone to swell. The resulting expansion of the silicone causes a mechanical actuator 16 to depress a low force mechanical membrane switch 18 to activate an impedance change.

After exposure, the silicone sheets are easily reset for continued use within the housing. Specifically, gasoline and other volatile liquids will evaporate from the silicone sheets over a period of time and the sensor sheets will reset themselves to their original dimensions. To the extent the sensor is exposed to diesel fuel and/or other less volatile liquids, the sensor can also be flushed with a solvent and then allowed to dry causing the internal components to return to their original dimensions. It has been found that the sensing membrane 34 of the present sensor can also be immersed in water for weeks and still respond to hydrocarbon. This specificity to hydrocarbons prevents "false alarms" if water or other non-hydrocarbon liquid contacts the sensor.

With reference now to FIGS. 1-4, a fluid sensor 10 for detecting hydrocarbons is provided. As may be seen in FIGS. 3 and 4, the fluid sensor is comprised of a sensor housing 12, a first sensor package 14, an actuator 16, and a switch 18. The sensor housing 12 includes a body portion 20 and a cap 24 that define an inner chamber 22 of the sensor housing 12. It is preferable that a portion of the inner surface of the housing 12 and a portion of the outer perimeter of the cap 24 include cooperative threading 26 so that the cap can be easily screwed onto the housing and removed from the housing. Accordingly, the cap 24 is removably attached to the body portion 20. Any suitable mechanism for removably attaching the cap 24 to the body portion 20 of the sensor housing 12 may be employed.

It is also contemplated that the cap 24 be permanently affixed to the body portion 20 of the sensor housing 12 without departing from the present invention.

In the embodiment of the invention in which the cap 24 is removably attachable from the body portion 20, a gasket, o-ring or other sealing mechanism 28 is employed to retard undesirable fluid entry past the edge of the switch 18. More specifically, it is undesirable for liquids to pass into the chamber 27 behind the switch and then through vent holes into the switch, as such liquids may damage the switch contacts. Preferably, the sealing mechanism is an epoxy.

In one embodiment of the present invention shown in FIG. 3, the cap 24 includes a plurality of apertures 30 therein. These apertures 30 allow for the ingress of suspected hydrocarbons or other fluids at issue into the chamber 22 formed by the body portion 20 and cap 24. Preferably, the cap 24 is configured to be unscrewed from the housing 12 via a thin lip that can be gripped by a user. The cap 24 may also include means 32 to allow a user to remove the cap 24 from the housing 12. For example, in one embodiment of the invention shown in FIG. 3, a slot is disposed in an outer surface of the cap 24. Accordingly, a user may unscrew the cap 24 from the body portion 20 of the housing 12 by use of a screwdriver, a coin, or other suitable tool. The means 32 may also be keyed so as to limit or restrict removing the housing to those with the proper, matching key. It will be understood that the cap 24 may not include a means 32, and may still comport with the present invention.

The sensor housing 12 can be made from any suitable material. However, it is preferable that at least the body portion 20 of the sensor housing 12 is formed from Delin® acetal homopolymer. The cap 24 forming the sensor housing 12 is preferably formed from Delrin® acetal homopolymer. It will be understood, however, that the sensor body portion 20 and cap 24 may be made from any suitable, generally non-porous, material used in connection with hydrocarbon sensing applications wherein degradation will not be an issue.

As shown more particularly in FIGS. 3 and 4, the sensor further includes a sensor package comprised of alternating sensing membrane layers 34 and screen layers 36. The sensor package is disposed within the sensor housing 12 and includes at least a pair of screens 36 and a sensing membrane 34 sandwiched between the screens 36. The screens 36 are provided to enhance the wicking characteristics of fluid entering in the housing to and across the membrane(s) 34 and decrease the response time of the sensor. The screens 36 are preferably formed from fiberglass, stainless steel or nylon. However, the screens 36 may be formed from any combination of these materials or, alternatively, of any material suitable to form a layer of wicking material that will not degrade when exposed to the fluids in the environment.

In one preferred embodiment of the present invention, the sensing membrane 34 is a silicone layer (or wafer) adapted to expand when exposed to a predetermined quantity of a hydrocarbon. Preferably the sensing membrane 34 has a thickness between approximately 0.010 to about 0.10 inches. However, it is contemplated that the sensing membrane 34 may be thicker or thinner depending on the size and volume of the sensor. According to one embodiment shown in FIG. 4, each sensing membrane 34 has an aperture therein. The aperture provides a shorter flow path for liquid to travel. The aperture also provides more consistent response times. Specifically, the aperture prevents the sensing membranes 34 from sealing the edges of the cavity, thereby preventing additional liquid from entering easily. The combination of the screens and aperture allow both sides of each layer of sensing membrane 34 to be exposed to the liquid very quickly. Preferably, the aperture in the silicone membrane has a diameter $D_s$ of about 0.0625 to about 0.125 inches. However, the sensing membrane 34 can include more than one aperture, depending on the fluid volume to which the sensor will be exposed. Accordingly, the diameter $D_s$ of the membrane may be smaller or larger as appropriate for the fluid volume.

In the embodiment discussed above, the sensor includes a first sensor package 14 and a second sensor package 38. The second sensor package 38 includes a third screen 36 and a fourth screen 36. The third and fourth screens 36 also have a sensing membrane 34 sandwiched therebetween. An intermediate sensing membrane 35 is sandwiched between the first screen 36 of the first sensor package 14 and the fourth screen 36 of the second sensor package 38. It is also contemplated that, in instances in which the sensor is being used to detect fluids other than hydrocarbons, the sensing membrane 34 may be of a material that is adapted to dissolve when exposed to a second predetermined fluid.

Referring now to FIGS. 3 and 4 again, the sensor further includes an actuator 16 and a switch 18. The actuator 16 is disposed within the cavity of the sensor housing 12 and proximate the sensor package. The actuator 16 is moveable between a first position and a second position through an intermediate position. The switch 18 is disposed within the housing 12 proximate the actuator 16.

The switch 18 is preferably a low-pressure membrane and operates between open and closed positions. The switch 18 can be a normally-open or normally-closed configuration. However, the preferred embodiment of the switch 18 is biased to a normally-closed position by a magnet 40 disposed between the actuator 16 and the switch 18. Although the biasing means is preferably a magnet 40, it can be any one of a number of mechanical biasing devices, such as a spring (e.g., a leaf spring, a coil spring, a tension spring, etc.). It is also contemplated that the switch 18 can also be biased to a normally-open position without departing from the present invention. However, it has been found that biasing the switch to a normally closed position is preferred because one can always and easily tell if the circuit is on and working properly by monitoring the circuit.

When the actuator 16 is in the second position, at least a portion of the actuator 16 moves the switch 18 from the closed position to the open position. According to the present invention, the switch 18 will have a relatively low activation force requirement. Preferably the activation force will be between 15 g and 50 g. However, these force requirements may vary with the size and volume of the sensor.

In one embodiment of the invention, the sensor further includes at least one vent opening. In one embodiment, a vent opening is disposed proximate a bottom surface of the switch 18 and below the switch. Because pipes and other environments wherein the sensor is to be placed have a pressure or vacuum therein, venting is permitted both behind and in front of the switch to equalize the pressure from the environment by venting or exposing the internal side of the membrane switch.

A hydrophobic and oleophobic sealing membrane is disposed over the external vent opening 41 to prevent liquids from entering the cavity 27 below switch 18 and subsequently switch 18 contact area. The sealing membrane is preferably made from hydrophobic and oleophobic materials sold under the trade name GORE™ Membrane Vents. However, any hydrophobic and oleophobic sealing material may be employed in connection with the present invention.

In another embodiment of the invention, the sensor 10 further includes at least one additional method of venting and stabilizing the sensor for use in pressurized applications. In some applications the GORE® Membrane Vents are used. At has been found that in other applications, when the vent sealing membrane is wet with certain oils, liquids, such as water, can enter through the membrane into the switch and cause problems over time with the electrical components of the switch. In order to reduce this potential issue, FIG. 5 shows additional components to form the fluid sensor 10 in the present invention. The sensor 10 further includes a pair of check valves 50,52 acting as an inlet check valve and an outlet check valve, respectively. Both the inlet and outlet check valves 50,52 are associated with the tubing 54. The tubing 54 and check valves 50,52 are contained within an extended probe housing 56 receiving the slightly tapered lower neck 58 of the housing 12 in tight sealed engagement therebetween. A gasket 60 seals off the air cavity or chamber 27 behind the switch 18 from the interior of the extended probe housing 56. A pair of tubes 62,64 extends from the air cavity 27 to the interior of the extended housing 56 and pass through the gasket 60. The portions of the tubes 62,64 extending into the housing 56 are connected to the check valves 50,52 via tubing 54. The inlet check valve 50 is generally located towards the rear end of the housing 56 with a single piece of tubing 54 connecting its output end 66 to the tube 62. The outlet check valve 52 is generally located with its input 68 in close proximity to the tube 64 and having the tubing 54 enclosing the space between the check valve 52 and tube 64. The outlet check valve 52 includes additional tubing 54 attached to its output end 70. The tubing 54 extends toward the rear of the housing 56 for venting purposes alongside and generally parallel to the input end 72 of the inlet check valve 50 at the rear of the housing 56.

When the piping system is initially pressurized, the inlet check valve 50 opens and allows air/nitrogen to enter the cavity 27. The check valve 50 has an opening pressure of approximately 0.5 psi so there is no more than a 0.5 psi difference between the internal and external pressures. Once pressure is stabilized, the inlet check valve closes and seals out liquids. The small pressure differential of 0.5 psi does not adversely impact upon the sensitivity of the sensor 10. When the containment pipe pressure is lowered, the outlet check valve 52 relieves the internal pressure in order to maintain the maximum 0.5 psi differential in the system. After the pressure stabilizes, the outlet check valve 52 closes to keep out liquids.

In addition, the rear end of the housing 56 includes a gasket 74 and an epoxy seal 76 with a pair of wire leads 78 connecting to the switch 18 (not shown inside the housing 56). The extended housing 56 further includes breather holes 80 of approximately 0.125 inches in diameter located at predetermined points on the circumference of the housing 56 to assist in the equalization of the pressure within the extended housing 56 during operation of the check valves 50,52.

As used herein, the terms "first," "second," "third," etc. are for illustrative purposes only and are not intended to limit the embodiments in any way. Additionally, the term "plurality" as used herein is intended to indicate any number greater than one, either disjunctively or conjunctively as necessary, up to an infinite number.

While the specific embodiments have been illustrated and described, numerous modifications come to mind without significantly departing from the spirit of the invention, and the scope of protection is only limited by the scope of the accompanying Claims.

What is claimed is:

1. A fluid sensor comprising:
   a sensor housing defining a sensing chamber;
   a first sensor package disposed within the sensor housing, the first sensor package comprising:
   a sensing membrane being adapted to expand when exposed to a predetermined quantity of a first predetermined fluid;
   an actuator disposed proximate the sensor package within the sensor housing, the actuator being moveable between a first position and a second position through an intermediate position; and,
   a switch disposed proximate the actuator and within the housing, the switch being operable between a closed position and an open position, wherein when the actuator is in the second position at least a portion of the actuator depresses the switch.

2. The sensor of claim 1, wherein the sensing membrane has a thickness $T_o$ between 0.010 to 0.10 inches.

3. The sensor of claim 1, wherein the sensing membrane is adapted to dissolve when exposed to a second predetermined fluid.

4. The sensor of claim 1, wherein the sensor housing comprises a body portion and a cap removably attached to the body portion, the cap including a plurality of apertures therein.

5. The sensor of claim 1, wherein at least one vent opening is disposed proximate a bottom surface of the switch.

6. The sensor of claim 1, further comprising a sealing membrane disposed over the vent opening, the sealing membrane having hydrophobic and oleophobic characteristics.

7. The sensor of claim 1, further comprising a means for biasing the switch to one of either the open position or the closed position.

8. The sensor of claim 7, wherein the means for biasing the switch is a magnet disposed between the actuator and the switch.

9. The sensor of claim 8, further comprising a first screen and a second screen, the sensing membrane being disposed between the first and second screens.

10. The sensor of claim 9, further comprising a second sensor package disposed within the sensor housing, the second sensor package comprising:
    a third screen and a fourth screen; and,
    a sensing membrane disposed between the third and fourth screens, the sensing membrane being adapted to expand when exposed to a predetermined quantity of the first predetermined fluid; and,
    an intermediate sensor membrane disposed between the fourth screen of the second sensor package and the first screen of the first sensor package.

11. A fluid sensor for detecting hydrocarbons, the fluid sensor comprising:
    a sensor housing, the sensor housing defining a sensing chamber and comprising a body portion and a cap portion;
    a sensor package disposed within the sensor housing, the sensor package comprising: a first screen and a second screen; and,
    a silicone membrane disposed between the first and second screens, the silicone membrane being adapted to expand when exposed to a predetermined quantity of a hydrocarbon and having at least one aperture therein, the at least one aperture defining a fluid path through the silicone membrane;
    an actuator disposed proximate the sensor package within the sensor housing, the actuator being moveable between a first position and a second position through an intermediate position; and,
    a switch disposed proximate the actuator and within the housing, the switch being operable between an open and closed position, the switch being biased to the closed position and wherein when the actuator is in the second position at least a portion of the actuator moves the switch from the closed position to the open position.

12. The sensor of claim 11, wherein the at least one aperture in the silicone membrane has a diameter $D_s=0.0625$ to 0.125 inches.

13. The sensor of claim 11, wherein the silicone membrane has a thickness $T_o$ between 0.010 to 0.1 inches.

14. The sensor of claim 11, wherein the first and second screens are one of either fiberglass, stainless steel and nylon.

15. The sensor of claim 11, further comprising a means for biasing the switch to the closed position.

16. The sensor of claim 15, wherein the means for biasing the switch is a magnet disposed between the actuator and the switch.

17. The sensor of claim 11, further comprising at least one vent opening disposed proximate a bottom surface of the switch.

18. The sensor of claim 17, further comprising a sealing membrane disposed over the vent opening, the sealing membrane having hydrophobic and oleophobic characteristics.

19. The sensor of claim 11, further comprising a second sensor package disposed within the sensor housing, the second sensor package comprising:
   a third screen and a fourth screen;
   a silicone membrane disposed between the third and fourth screens, the silicone membrane being adapted to expand when exposed to a predetermined quantity of hydrocarbon and having at least one aperture therein permitting fluid to pass therethrough; and,
   an intermediate silicone membrane disposed between the fourth screen of the second sensor package and the first screen of the first sensor package, the intermediate silicone membrane being adapted to expand when exposed to a predetermined quantity of a hydrocarbon and having at least one aperture therein permitting fluid to pass therethrough.

20. The sensor of claim 17, wherein the vent further comprises an extended housing used in a pressurized piping system attached to the distal end of the sensor housing body, a pair of check valves located within the extended housing serving as inlets and outlets to stabilize pressure within the fluid sensor, a pair of tubes and tubing associated with the check valves connecting the extended housing to approximately the bottom surface of the switch in a generally sealed relationship to prevent moisture from entering a predetermined air cavity behind the switch and a gasket positioned between the air cavity and the extended housing to separate the air cavity from the interior of the extended housing wherein the tubes pass through the gasket to connect the check valves with the air cavity.

21. The sensor of claim 20, wherein the extended housing includes a breather hole at a predetermined location on the extended housing to cooperate with the operation of the check valves and a gasket and a sealable material at a distal end opening of the extended housing to seal the housing from moisture and dust elements.

22. The sensor of claim 20, wherein the inlet and outlet check valves have a differential opening pressure of 0.5 psi so there will be no more than a 0.5 psi differential between the internal and external pressures in the sensor when the piping system is initially pressurized or later de-pressurized during operation.

* * * * *